United States Patent [19]

Heintz

[11] Patent Number: 5,720,078

[45] Date of Patent: Feb. 24, 1998

[54] DEVICE FOR ASPIRATING FLUIDS FROM HOSPITAL OPERATING ROOM FLOOR

[76] Inventor: J. Aaron Heintz, 26 Primrose Dr., Richboro, Pa. 18954

[21] Appl. No.: 814,563

[22] Filed: Mar. 11, 1997

Related U.S. Application Data

[63] Continuation-in-part of Ser. No. 615,569, Mar. 12, 1996, Pat. No. 5,655,258.

[51] Int. Cl.$^6$ ........................................... A47L 9/02
[52] U.S. Cl. ........................................... 15/415.1; 604/317
[58] Field of Search ........................... 15/322, 415.1, 15/417, 420, 422; 604/313, 317, 902

[56] References Cited

U.S. PATENT DOCUMENTS

| | | | |
|---|---|---|---|
| 1,054,052 | 2/1913 | Stewart | 15/415.1 |
| 2,235,224 | 3/1941 | Lofgren | 15/420 |
| 2,816,664 | 12/1957 | Haynes . | |
| 2,966,694 | 1/1961 | Brown . | |
| 3,520,300 | 7/1970 | Flower | 604/902 |
| 3,605,171 | 9/1971 | Candor et al. . | |
| 3,705,437 | 12/1972 | Rukavina, Jr. et al. . | |
| 4,041,569 | 8/1977 | Petersen . | |
| 4,156,948 | 6/1979 | Chauvier et al. . | |
| 4,243,214 | 1/1981 | LaRooka . | |
| 4,279,057 | 7/1981 | Restivo | 15/415.1 |
| 4,679,590 | 7/1987 | Hergenroeder . | |
| 4,718,653 | 1/1988 | Rothman . | |
| 4,729,146 | 3/1988 | Barr | 15/415.1 |
| 4,729,404 | 3/1988 | Hergenroeder . | |
| 5,014,389 | 5/1991 | Ogilvie et al. | 15/415.1 |
| 5,032,184 | 7/1991 | Ogilvie . | |
| 5,211,639 | 5/1993 | Wilk | 604/313 |
| 5,215,539 | 6/1993 | Schoolman | 604/313 |
| 5,267,370 | 12/1993 | Worwag . | |
| 5,295,982 | 3/1994 | Schatz | 604/313 |
| 5,437,651 | 8/1995 | Todd et al. | 15/420 |
| 5,655,258 | 8/1997 | Heintz | 15/415.1 |

FOREIGN PATENT DOCUMENTS

875054  7/1971  Canada ........................... 15/420

*Primary Examiner*—Terrence Till
*Attorney, Agent, or Firm*—Caesar, Rivise, Bernstein, Cohen & Pokotilow, Ltd.

[57] ABSTRACT

A suction device for removing liquids from a surface such as a floor. The device includes an air chamber formed from a top and a bottom plate, each of the plates having a respective top and bottom surface. The air chamber is in fluid communication with a fitting adjacent thereto. The bottom plate includes a plurality of holes therethrough. The bottom surface of the bottom plate additionally includes fabric adjacent thereto and feet to hold the bottom plate of the device up off the floor to enable fluid to be suctioned through the bottom plate holes and into the chamber via a conventional source of suction. The device is also arranged to be located beneath an area where fluid is escaping for directly receiving and evacuating fluid that would otherwise fall on the floor.

27 Claims, 5 Drawing Sheets

DEVICE FOR ASPIRATING FLUIDS FROM HOSPITAL OPERATING ROOM FLOOR

BACKGROUND OF THE INVENTION

This application is a Continuation-In-Part of my earlier filed U.S. patent application Ser. No. 08/615,569, filed on Mar. 12, 1996 now U.S. Pat. No. 5,655,258, whose entire disclosure is incorporated by reference herein. The present invention relates to an apparatus to remove fluid that drains or spills onto the floor during surgery.

During surgery waste fluids of various types find their way to the floor of the operating room. For example, during arthroscopic surgery sterile fluid (e.g., saline) is supplied to the surgical site. This fluid, if permitted to drain uncontrolled to the floor, presents an additional hazard.

A prior art approach toward solving this problem is disclosed in U.S. Pat. Nos. 4,679,590 and 4,729,404. These patents disclose a rubber mat to be placed beneath a surgical site in sealed engagement with the floor. The top surface of the mat is configured as multiple inverted pyramidal elements configured to collect fluid and direct it to a drain hole on the bottom side of the mat. The bottom side of the mat is provided with flow channels that become sealed to the floor and converge to a common suction port adapted for connection to a source of suction that is commonly available at wall-mounted suction ports in surgical operating rooms. The suction delivers the recovered fluid to a canister for disposal.

The suction mat arrangement described above appears unable to drain the rather significant amount of fluid that falls to the floor beyond the mat periphery. During arthroscopic surgery the sterile fluid delivered to the surgical side is often delivered at relatively high pressures, thereby making it difficult, if not impossible, for surgical personnel to direct the fluid so that, after flowing from the surgical site, it falls on the suction mat.

There are commercially available vacuum cleaners with movable suction heads adapted to draw liquid from floors toward a waste collection chamber. These devices, however, are not suitable for surgical environments for a number of reasons, not the least of which is the fact that the vacuum cleaner suction head must be manipulated by hand in order to be positioned at various spillage locations on the floor. Since the hands of operating room personnel are otherwise occupied during a surgical procedure, the use of a commercial vacuum cleaner would require additional personnel, thereby adding to the already high cost of surgery. Moreover, commercially available vacuum cleaners have built-in vacuum sources that are extremely noisy, thereby rendering communication between the surgeon and nurses difficult at best. It would be far more desirable to use a low level suction source (e.g., on the order of 300 millimeters of mercury below atmosphere pressure) such as is commonly available at a wall port in operating rooms; however, suction heads employed with commercial vacuum cleaners are incapable of operating at such low pressures.

Finally, the fluids that spill onto the floor during a surgical procedure are likely to be or become contaminated. Commercially available vacuum cleaner heads for liquids are not designed to be disposable after use and, accordingly, would become contaminated and present a health hazard.

In U.S. Pat. Nos. 5,032,184 and 5,014,389 (Ogilvie et al.) is disclosed a method and apparatus having a suction head for use in removing waste fluids from surgical operating room floors. The apparatus has a planar, low-friction bottom surface adapted to slide along the floor in response to translational forces applied by the foot of a surgeon, nurse or other surgery personnel. Flow channels recessed in the bottom surface extend from the periphery of the suction head to the mouth of a common suction port adapted for connection by flexible tubing to a waste fluid collection container or canister. The canister is also connected by means of a hose to a wall mounted suction port providing a negative low pressure on the order of 300 millimeters of mercury below atmospheric pressure. In the preferred embodiment, the suction head is a thin one-piece molded plate, preferably of resilient plastic material having a heat distortion temperature less than 270° F., so as to be sufficiently inexpensive to be discarded after each surgical procedure. The common suction port is defined as a tubular hose fitting extending upwardly from the top surface of the plate. Multiple support ribs extend along the top surface from the hose fitting to the suction head periphery in juxtaposition with respective flow channels to reinforce the flow channels against collapse and flow blockage.

Unlike the Ogilvie device, in the present invention, the barbed fitting exits the device at the side, so as to minimize a potential trip hazard in a surgical environmental which is typically encumbered with several fluid, electrical, and other lines.

Other patents showing suction devices and/or floor drainers include U.S. Pat. No. 2,966,694 (C. L. Brown, Jr.), U.S. Pat. No. 2,816,664 (R. H. Haynes), U.S. Pat. No. 3,605,171 (R. R. Candor et al.), U.S. Pat. No. 4,041,569 (Petersen), U.S. Pat. No. 4,156,948 (Chauvier et al.) and U.S. Pat. No. 5,267,370 (Worwag).

BRIEF SUMMARY OF THE INVENTION

These and other objects of this invention are achieved by providing a suction device for removing liquids from a surface such as a floor. The device includes an air chamber formed from a top and a bottom plate, each of the plates having a respective top and bottom surface. The air chamber is in fluid communication with a fitting adjacent thereto. The bottom plate includes a plurality of holes therethrough. The bottom surface of the bottom plate additionally includes fabric adjacent thereto and feet to hold the bottom plate of the device up off the floor to enable fluid to be suctioned through the bottom plate holes and into the chamber via a conventional source of suction. The device is also arranged to be located beneath an area where fluid is escaping for directly receiving and evacuating fluid that would otherwise fall on the floor.

BRIEF DESCRIPTION OF THE DRAWINGS

Other objects and many attendant features of this invention will become readily appreciated as the same becomes better understood by reference to the following detailed description when considered in connection with the accompanying drawings wherein.

DETAILED DESCRIPTION OF THE INVENTION

Figure 1:
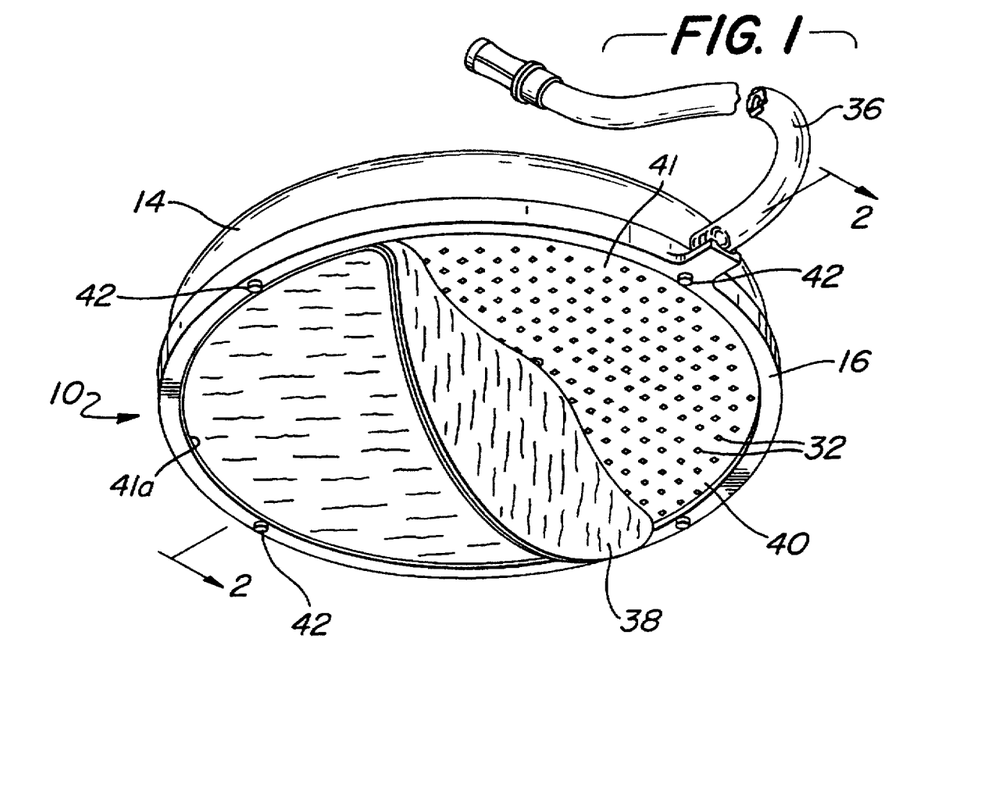
FIG. 1 is a bottom view of the device of the present invention showing the fabric of the bottom plate partially removed.

Referring now to various figures of the drawings where like reference numerals refer to like parts, there is shown at 10 in FIG. 1, a device constructed in accordance with this invention.

Figure 2:
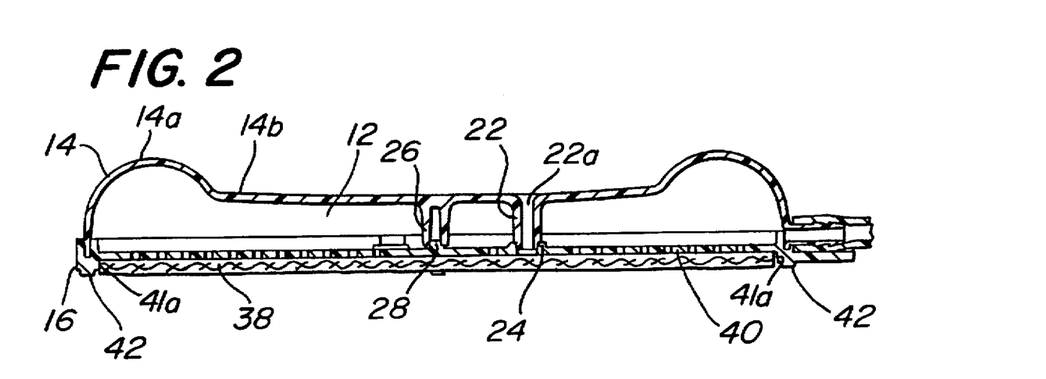
FIG. 2 is a cross-sectional view of the device of FIG. 1, taken along line 2—2 of FIG. 1.

The device 10 of the present invention consists of an air chamber 12 shown in FIG. 2, approximately 8 to 10 inches in diameter and ¾ to 1½ inches thick. The air chamber 12 is shown in a generally circular configuration, although any suitable shape may be utilized. The chamber 12 has top and bottom sections. In the preferred embodiment the chamber 12 is formed from a top plate 14 and a bottom plate 16, which can be either bonded or snapped together. However, integral construction is not excluded.

The device 10 is formed of acrylonitrile butadiene styrene (ABS) plastic or could be made of high-impact polystyrene (HIPS) plastic or any other suitable semi-rigid thermoplastic material.

Figure 3:
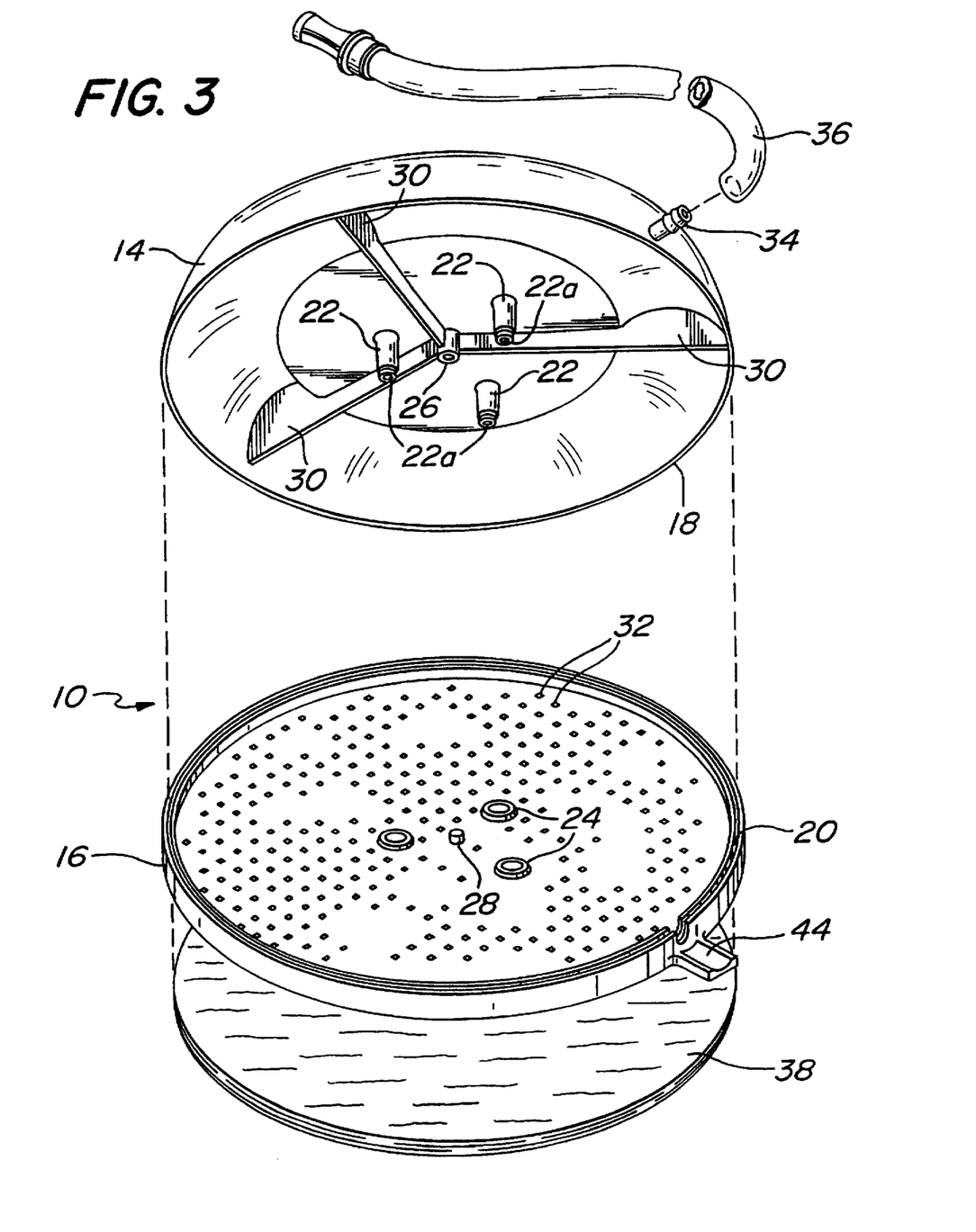
FIG. 3 is an exploded view of the device of FIG. 1.

As shown in FIG. 3, the top plate 14 has a cooperative circumferential edge 18 for example, which may be secured in a tapered rim, forming a self sealing air lock (tapered fit) into the cooperative mating edge 20 of bottom plate 16. In order to aid in the tapered fit of the top plate 14 to the bottom plate 16, the top plate 14 includes depending members 22 which cooperatively fit within respective recesses 24 located in bottom plate 16. The top plate 14 may also include receptacle 26 which is secured (e.g., ultrasonic welded, glued, etc.) to cooperative member 28 of bottom plate 16 shown in FIG. 3. The top plate 14 may further include radial stiffening ribs 30 as shown in FIG. 3 and may still further have one or more depressions in its top surface or a single large depression in its center to collect liquid or provide a place to permit receipt of the tip of a shoe of a person to move the device.

As shown in FIGS. 1 and 3, the bottom plate 16 also has a disc with a plurality of small holes 32, typically 0.030 to 0.250 inches in diameter, which communicate from the bottom (fluid source) of the device 10 to the air chamber 12 inside the device 10. The air chamber 12, in turn, communicates with a barbed fitting 34 and the suction line 36 which is connected to a conventional vacuum source (not shown). The plurality of small holes 32 permit the suction and/or transmission of fluid (not shown) therethrough.

As shown in FIGS. 1 and 2, a disk 38 of preferably absorbent, woven or non-woven fabric is applied to the bottom 40 of the bottom plate 16. The fabric could be constructed exclusively of a polypropylene blown material or exclusively of a cellulose blown material, cellulose sponge or, alternatively, of a polypropylene/cellulose blend. Moreover, the fabric could be constructed of any other suitable absorbent material. The fabric acts as a sound baffling mechanism to reduce the annoying distraction of the suction noise.

As shown in FIGS. 1 and 2, the bottom plate 16 also has several small (0.010 to 0.12 inch high) "feet" 42 which hold the device 10 up off the floor. The purpose for this is twofold. The feet 42 hold the suction holes 32 up off the floor so as to avoid having the device 10 sucked down onto the floor and rendered difficult to move. Secondly, the feet 42 allow the device 10 to be kicked by operating room personnel into a puddle without significant splashing of surrounding fluid (not shown). The device 10 will skim across the top of the puddle with minimal disruption (splashing) to the fluid, providing increased safety to the clinicians. Furthermore, the height of a puddle of fluid on a concrete, linoleum, or similar slick construction materials is a relatively constant one, dictated by the surface tension, density, and viscosity of the water. The height of the feet 42 is optimized to take best advantage of this known height (approximately 0.5 to 0.9 times the height of a typical puddle).

As shown in FIG. 3, the barbed fitting 34 is arranged to fit within a recess located in the bottom plate 16 to form a lower reservoir for the collection of fluids. This lower reservoir is actually located adjacent the disk having the plurality of small holes 32. In the preferred embodiment (FIG. 3), the barbed fitting 34 is integral with the top plate. While the conventional vacuum source (not shown) does provide a dynamic pressure to pull the fluids into the suction line 36, fluid will also flow into the lower reservoir by operation of gravity due to the location of the barbed fitting 34. Additionally, the bottom plate 16 is provided with a strain limiter 44 that acts to prevent the barbed fitting 34 from breaking off from the top plate 14 in the event the barbed fitting 34 is accidentally kicked or stepped on during use of the device 10 in the operating room.

The device 10 of the present invention facilitates aspiration of fluids from a surgical operating room. The device 10 easily slides across the floor upon being kicked, so as to be moved to puddles of spilled fluids. While the device 10 could be used in almost any surgical procedure, it is most applicable for those procedures which use a large amount of irrigation solution (typically saline or other water-based solutions). These procedures, such as arthroscopy (joint surgery) and cystoscopy (surgery of the urinary tract) and hysteroscopy (surgery of the uterus) can use up to twenty liters of fluid, most of which is typically spilled on the floor.

The device of the present invention can be attached to the built-in suction source present in nearly every operating room. An intermediate canister (not shown) is typically employed as a fluid trap to avoid contamination of the vacuum lines and pump.

The present invention may be supplied with pre-attached tubing for convenience, but could also be supplied without tubing.

In an alternate form of the invention, the bottom plate 16 of air chamber 12 may be finely porous, with more and smaller holes 32, such that the fabric disk is dispensed with.

Referring again to FIGS. 2 and 3, in addition to aspirating fluids that have already fallen onto operating room floors, the preferred embodiment 10 is arranged to be placed directly under a primary source of dripping or streaming fluid at the surgical site to effectively collect fluid that would otherwise fall onto the floor and evacuate that fluid through flexible tubing to a waste fluid collection container or canister.

To effectuate disposal of fluid in this manner, the top surface of the top plate 14 is provided with a rounded outer rim 14a that surrounds one or more depressions 14b or a single large depression in the center of the top plate 14. Together, the rim 14a and depressions 14b form a dimple that acts to receive fluid that has fallen from the operating table and direct that fluid toward a plurality, e.g., three, of depending members 22.

As best shown in FIG. 2, each depending member 22 cooperatively fits within respective recesses 24 located in bottom plate 16 to form a plurality of enclosed tunnels 22a. As best shown in FIG. 2, each enclosed tunnel 22a is actually isolated from the internal chamber 12 that surrounds it. However, it should be pointed out at this juncture that isolation of the tunnels 22a from the internal chamber is not critical to the operation of the device 10. If, for example, the outer wall of each tunnel 22a were provided with a plurality of openings communicating directly with the internal chamber, the device 10 would operate in its intended manner. Further, if instead of tunnels 22a, the top plate 14 of the device 10 were provided with through openings that communicated directly with the internal chamber 12, the device 10 would operate in its intended manner. In other words, it is not critical to the operability of the device 10 that the tunnels 22a be isolated from the internal chamber.

As best shown in FIGS. 1 and 2, based upon the construction of the device 10, the bottom 40 of bottom plate 16 is actually held up off the floor (not shown). The space below the bottom plate 16 forms a mouth 41 defined by the bottom 40 of the bottom plate 16 and inner surface 41a. As shown in FIGS. 1 and 2, the mouth 41 is occupied by the disk 38 which acts as a fluid conducting member. Each enclosed tunnel 22a permits fluid to pass by operation of gravity from the top surface 14b downwardly into the mouth 41. Each enclosed tunnel 22a actually performs its intended function within a range between 0.15 and 0.30 inches in diameter, however, could be larger.

In accordance with one aspect of this invention, the fluid conducting member 38 is located in the mouth for the purpose of soaking up fluid that passes through each enclosed tunnel 22a and enabling the fluid to be conducted into the air chamber. As shown in FIG. 1, the fluid conducting member 38 is shown as being without a central opening. In an alternative embodiment (not shown), the fluid conducting member 38 is circular and has a central opening. Thereafter, the conventional vacuum source (not shown) provides a dynamic pressure, i.e., negative pressure, to pull the fluid out of the fluid conducting member 38 and through the small suction holes 32 of the bottom plate 16 and into the suction line 36 which delivers the recovered fluid to a canister for disposal. It should be pointed out at this juncture that in accordance with the invention, the use of the fluid conducting member 38 is optional and the device 10 is fully operative in the absence of the fluid conducting member 38, however, without the fluid conducting member 38, the device 10 is somewhat noisier during operation.

It should also be pointed out at this juncture that under the earlier filed patent application, U.S. patent application Ser. No. 08/615,569 now U.S. Pat. No. 5,655,258, filed on Mar. 12, 1996, the suction holes 32 were specified as being typically 0.040 to 0.090 inches in diameter. Subsequently, it has been determined that the suction holes 32 actually perform their intended function within a range between 0.030 to 0.250 inches in diameter. In addition, in the originally filed patent application, the feet 42 were specified as being within a range of 0.040 to 0.90 inches in height. Subsequently, it has been determined that the feet 42 actually perform their intended function from 0.010 to 0.12 inches in height. Further, in the originally filed patent application, the fluid conducting member 38 was described as a fabric typically constructed of a polypropylene/cellulose blend for maximum absorbency and sound baffling. Subsequently, it has been determined that any suitable absorbent material, not necessarily in blown, woven or in sponge forms, could be utilized in constructing the fluid conducting member 38, e.g., polypropylene, cellulose or a polypropylene/cellulose blend. It should be pointed out at this juncture that it is not essential that the fluid conducting member 38 be formed of an absorbent material so long as the fluid conducting member permits the passage of fluid therethrough. The fluid conducting member 38 can be formed in any one of a number of different shapes, circular, square, rectangular, etc., based upon the outer contour of the device under which it is placed.

Figure 4:
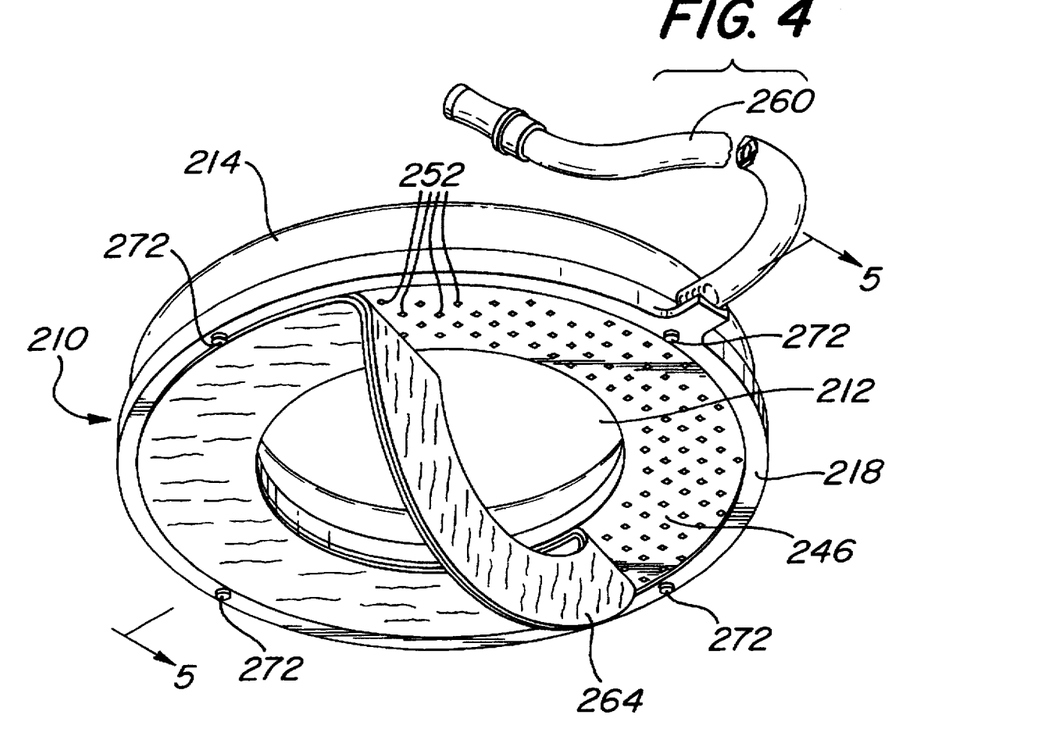
FIG. 4 is a bottom view of a second embodiment of the device of the present invention showing the fabric of the bottom plate partially removed.
Figure 5:
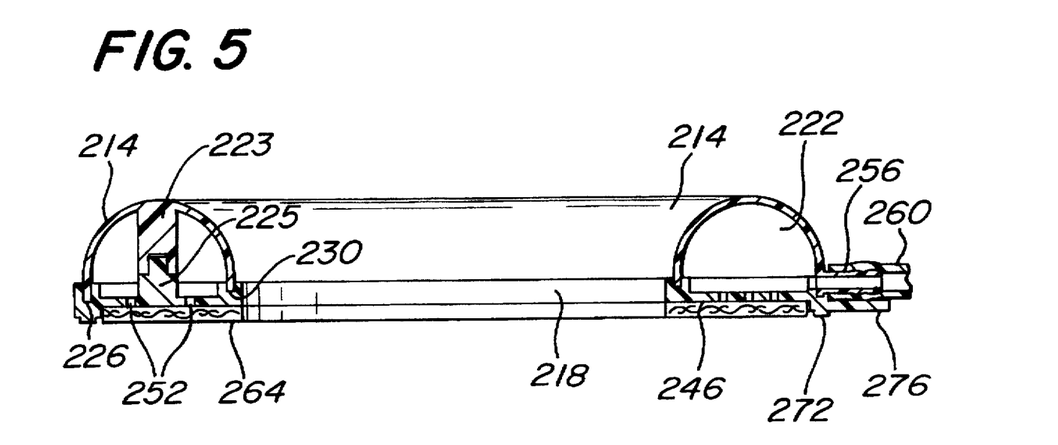
FIG. 5 is a cross-sectional view of the device of FIG. 4, taken along line 5—5 of FIG. 4.

Referring now to FIGS. 4 and 5, there is shown at 210 a second embodiment of a device for aspirating fluids from a hospital operating room floor. As is the preferred embodiment, the second embodiment is a dual function device, i.e., it is arranged for aspirating fluids from a surgical operating room floor and is also arranged to be placed directly under a primary source of dripping or streaming fluid at the surgical site to effectively collect fluid that would otherwise fall onto the floor and evacuate that fluid through flexible tubing to a waste fluid collection container or canister. Basically, the second embodiment device 210 is a ring-shaped structure that has a generally circular outer dimension and includes a central aperture 212 or hole extending therethrough. The device 210 has an top plate 214 and a bottom plate 218 that together form an annular internal chamber 222 (FIG. 5).

Figure 6:
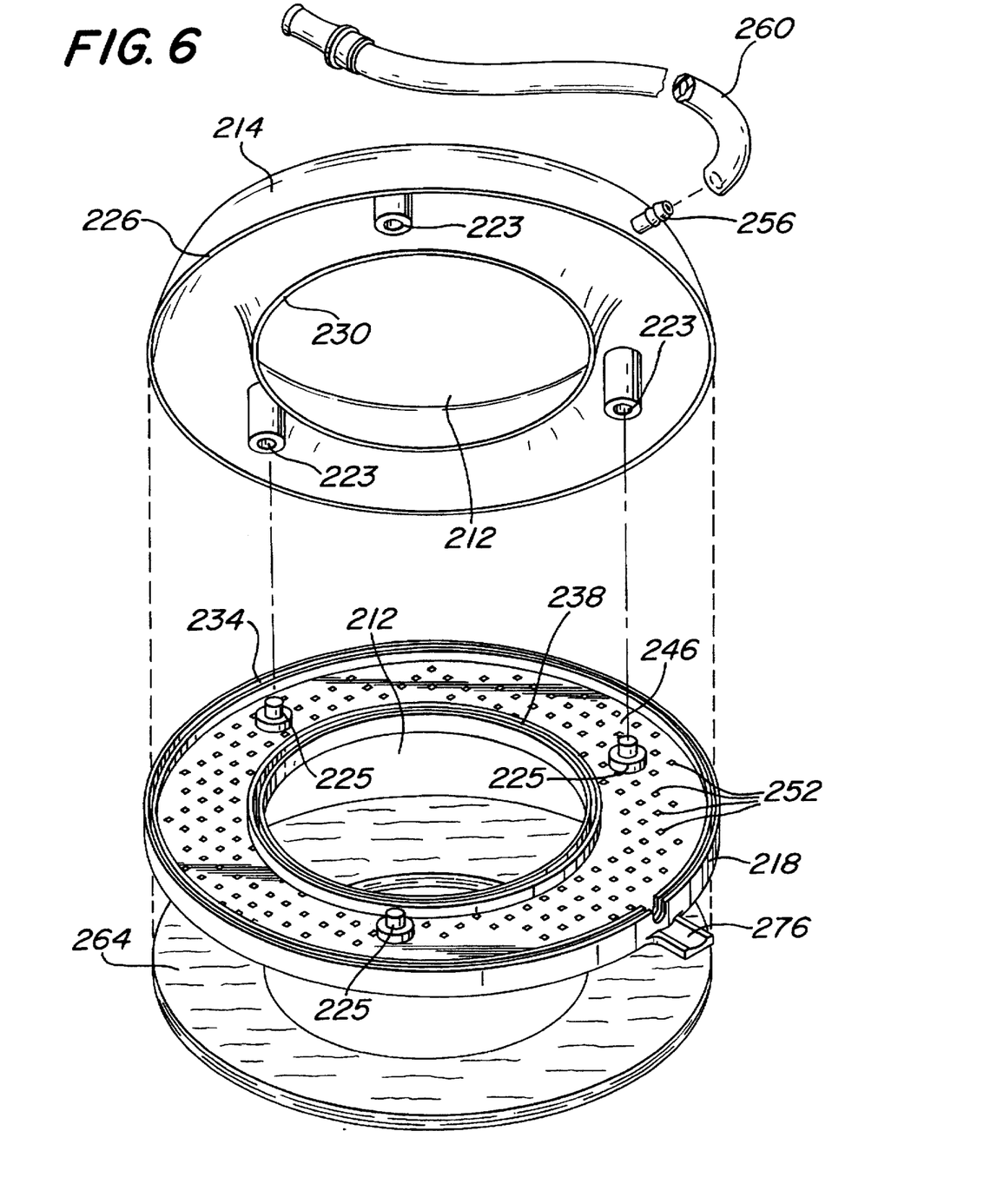
FIG. 6 is an exploded view of the device of FIG. 4.

Referring now to FIG. 6, the top plate 214 is provided with an outer circumferential edge 226 and an inner edge 230. The outer circumferential edge 226 is tapered and arranged to frictionally fit within a cooperative outer receiving channel 234 of the bottom plate 218. Likewise, the inner edge 230 is also tapered and arranged to frictionally fit within a cooperative inner receiving channel 238 of the bottom plate 218. As best shown in FIG. 6, upon insertion of the tapered edges 226 and 230 of the top plate 214 into the receiving channels 234 and 238, respectively, of the bottom plate 218, a self-sealing air lock is formed which eliminates any need for sealing adhesives, caulks or gasketing. As best shown in FIGS. 5 and 6, the top plate 214 includes depending female components 223 which cooperatively fit within respective male components 225 located in bottom plate 218 and are secured therein by any suitable means, e.g., ultrasonic welding, gluing, etc.

Alternatively, rather than being described as comprising top and bottom plates, the device 210 could be of integral construction. In the second embodiment 210 both the top and bottom members are made of acrylonitrile butadiene styrene (ABS) plastic or could be made of high-impact polystyrene (HIPS) plastic or any other suitable semi-rigid thermoplastic material.

Together, the top and bottom plates of the device 210 form a sealed air chamber 222 as shown in FIG. 5. The air chamber 222 is annular in shape and surrounds the central aperture 212 which is approximately 4 inches in diameter, however, could be smaller or larger, e.g., between three and five inches in diameter. The sealed air chamber 222 is approximately ¾ to 1½ inches thick at its maximum cross-sectional dimension and the annular ring is approximately 8 to 10 inches in diameter, however, these dimensions are not critical to the operation of the invention and other dimensions could be employed. The sealed air chamber 222 is shown in a generally semi-circular configuration in cross-section as shown in FIG. 5, however, any suitable shape may be utilized.

As shown in FIGS. 4 and 6, the bottom plate 218 comprises a circular member 246 with a plurality of small suction holes 252, typically 0.030 to 0.25 inches in diameter. As best shown in FIG. 4, the member 246 is actually held up off the floor (not shown). The space below the member 246 forms a mouth of the device 210 which is shown as being occupied by a fluid conducting member 264. The aperture 212 enables fluid to pass by operation of gravity from the top plate downwardly into the mouth. The air chamber 222 communicates with a barbed fitting 256 and a suction line 260 which is connected to a conventional vacuum source (not shown). The plurality of small holes 252 permit the suction and/or transmission of fluid (not shown) from the mouth into the air chamber.

As shown in FIGS. 4 and 6, the fluid conducting member 264, formed of any suitable fabric, including but not limited to absorbent materials, is located within the mouth under the bottom surface 246 of the bottom plate 218. As shown in FIGS. 4 and 6, the fluid conducting member 264 is ring-shaped and has a central circular opening that corresponds in size with the central aperture 212. In an alternative embodiment (not shown), the fluid conducting member 264 could be solid throughout (without a central opening). The fluid conducting member 264 is constructed of either an absorbent material, e.g., a polypropylene material, a cellulose material or of a polypropylene/cellulose blend, or other absorbent materials, or a nonabsorbent material that permits the passage of fluid therethrough. Using these materials, the fluid conducting member 264 acts additionally as a sound baffling mechanism to reduce the annoying distraction of the suction noise.

As shown in FIGS. 4 and 5, the bottom plate 218 also has several small (0.010 to 0.12 inch high) "feet" 272 which hold the device 210 up off the floor. These feet 272 serve the same two-fold purpose as described above in connection with the feet 42 of the preferred embodiment, i.e., to hold the bottom plate of the device up off the floor to enable fluid to be suctioned through the bottom plate holes and into the chamber via a conventional source of suction.

As best shown in FIG. 6, the barbed fitting 256 is arranged to fit within a recess located in the bottom plate 218 to form a lower reservoir for the collection of fluids. This lower reservoir is actually located adjacent the circular member 246. In the second embodiment (FIG. 6), the barbed fitting 256 is integral with the top plate 214. While the conventional vacuum source (not shown) does provide a dynamic pressure to pull the fluids into the suction line 260, fluid will also flow into the lower reservoir by operation of gravity due to the location of the barbed fitting 256. Additionally, the bottom plate 218 is provided with a strain limiter 276 that acts to prevent the barbed fitting 256 from breaking off from the top plate 214 in the event the barbed fitting 256 is accidentally kicked or stepped on during use of the device 210 in the operating room.

As previously stated, the device 210 of the present invention operates in two ways. First, it may be used to facilitate the aspiration of fluid puddles from a surgical operating room floor in the manner described in connection with the preferred embodiment device 10. That is, the device 210 easily slides across the surgical operating room floor upon being kicked, so as to be moved over puddles of spilled fluids. Thereafter, the puddle is soaked up into the fluid conducting member located below the annular internal chamber 222. The conventional vacuum source (not shown) provides a dynamic pressure to evacuate the fluid out of the fluid conducting member 264 and through the small suction holes 252 of the bottom plate 218 and into the suction line 260. Because during operation, the fluid conducting member 264 is subjected to vacuum pressure, it remains in a less than fully saturated condition and therefore continues to soak up any remaining fluid in the puddle.

Secondly, during the course of a surgical procedure, a significant amount of fluid falls directly from the operating table onto the floor. The device 210 of the present invention may be located directly under a primary source of dripping or streaming fluid at the surgical site for the purpose of capturing the fluid directly and evacuating it. In particular, as best shown in FIGS. 5 and 6, the top plate 214 is formed of an annular rounded surface that surrounds the central aperture 212. Once placed under a primary source of dripping or streaming fluid, the annular rounded surface of the top plate 214 acts to directly receive that fluid and direct or conduct it through the central aperture 212 where it is soaked up into the fluid conducting member 264 located below the annular internal chamber 222. Thereafter, the conventional vacuum source (not shown) provides a dynamic pressure to pull the fluid out of the fluid conducting member 264 and through the small suction holes 252 of the bottom plate 218 and into the suction line 260.

The device 210 can be attached to the built-in suction source present in nearly every operating room. An intermediate suction canister, e.g., usually one to three liters in size or larger, (not shown) is typically employed as a fluid trap to avoid contamination of the vacuum lines and pump. The present invention may be supplied with pre-attached tubing for convenience, but could also be supplied without tubing.

While the device 210 could be used in almost any surgical procedure, it is most applicable for those procedures which use a large amount of irrigation solution (typically saline or other water-based solutions). These procedures, such as arthroscopy (joint surgery) and cystoscopy (surgery of the urinary tract) and hysteroscopy (surgery of the uterus) can use up to twenty liters of fluid, most of which can typically be spilled on the floor.

Figure 7:
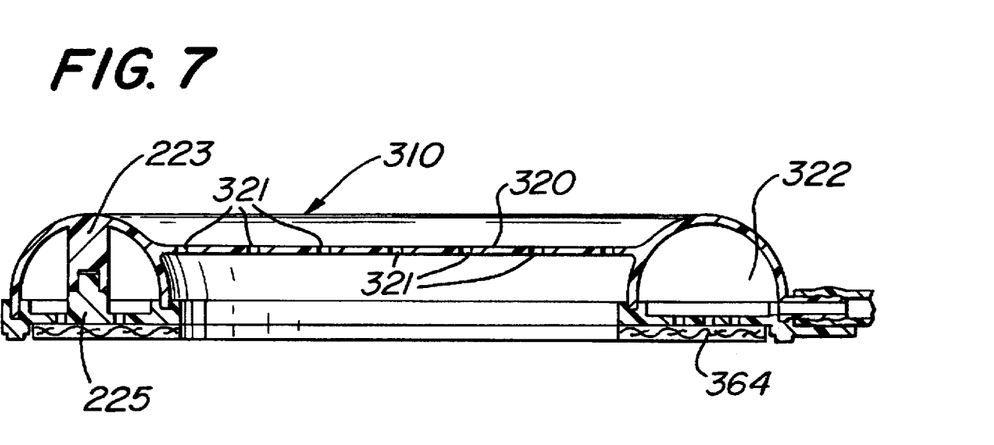
FIG. 7 is a cross-sectional view of a third embodiment of the device of the present invention.

Referring now to FIG. 7, there is shown a third embodiment 310 device for aspirating fluids from a hospital operating room floor. The device 310 is a dual function device, i.e., it is arranged for aspirating fluids from a surgical operating room floor and is also arranged to be placed directly under a primary source of dripping or streaming fluid at the surgical site to effectively collect fluid that would otherwise fall onto the floor and evacuate that fluid through flexible tubing to a waste fluid collection container or canister. The device 310 is similar in construction to the device 210 shown in FIGS. 4 through 6 in that it is a ring-shaped structure that has a generally circular outer dimension. However, the device 310 additionally comprises a platform 320 that extends across the central aperture. The platform is provided with a plurality of perforations 321 to allow fluid to flow through to where it is soaked up into a fluid conducting member 364 located below the annular internal chamber 322. Thereafter, the conventional vacuum source (not shown) provides a dynamic pressure to pull the fluid out of the fluid conducting member 364 and into the suction line.

Without further elaboration the foregoing will so fully illustrate my invention that others may, by applying current or future knowledge, adapt the same for use under various conditions of service.

I claim:

1. A floor engaging moveable suction device for directly receiving and evacuating fluid, said device arranged to be located beneath an area where fluid is escaping, said device comprising:

a. a center portion and a bottom means located at the center portion of the device for directly receiving fluid from the area directly above said device, b. said receiving means including fluid conducting means for communicating received fluid from said receiving means to a mouth located at the bottom of the device;

c. a discharge port communicating with said mouth, said discharge port being constructed and arranged to connect with a vacuum source by means of a suction line; and, d. an outer surface defining means to permit the device to be kicked to different locations on the floor.

2. The device of claim 1 wherein said device is also arranged for aspirating fluid from a floor, said mouth being located proximate to the floor to enable the device to aspirate the fluid therefrom.

3. The device of claim 1 additionally comprising an air chamber, said discharge port being disposed on said air chamber and said mouth being in communication with said air chamber.

4. The device of claim 3 wherein said fluid conducting means comprises a central aperture extending from said receiving means to said mouth, and wherein said air chamber is annular in shape and surrounds said central aperture.

5. The device of claim 4 wherein said central aperture is between three and five inches in diameter.

6. The device of claim 3 wherein said air chamber is defined by a top plate and a bottom plate secured together.

7. The device of claim 6 wherein said bottom plate comprises a plurality of small holes in fluid communication with said air chamber.

8. The device of claim 7 wherein each of said holes is between 0.030 to 0.250 inches in diameter.

9. The device of claim 6 wherein said top and bottom plates are formed of ABS plastic.

10. The device of claim 6 wherein said top and bottom plates are formed of high-impact polystyrene.

11. The device of claim 6 wherein said top plate additionally comprises an outer circumferential edge and wherein said discharge port is secured to said edge.

12. The device of claim 6 wherein said top and bottom plates are formed of a semi-rigid thermoplastic material.

13. The device of claim 6 wherein said top plate additionally comprises a top surface and wherein said receiving means is disposed on said top surface.

14. The device of claim 6 wherein said top and bottom plates are of integral construction.

15. The device of claim 3 wherein said fluid conducting means is isolated from said air chamber.

16. The device of claim 1 wherein said fluid conducting means comprises a plurality of enclosed tunnels extending from said receiving means to said mouth.

17. The device of claim 16 wherein each enclosed tunnel is between 0.15 and 0.30 inches in diameter.

18. The device of claim 1 additionally comprising floor contacting feet extending away from said device to hold said device up and away from contact with the floor.

19. The device of claim 18 wherein each of said feet is between 0.010 to 0.12 inches in length.

20. The device of claim 1 additionally comprising a fluid conducting means secured against the bottom of said device.

21. The device of claim 20 wherein said fluid conducting means is formed of an absorbent material.

22. The device of claim 20 wherein said fluid conducting means is formed of a polypropylene/cellulose blend.

23. The device of claim 20 wherein said fluid conducting means is formed of a polypropylene blown material.

24. The device of claim 20 wherein said fluid conducting means is formed of a cellulose blown material.

25. The device of claim 20 wherein said fluid conducting means is formed of a cellulose sponge.

26. The device of claim 20 wherein said fluid conducting means further comprises a circular opening in the center thereof.

27. The device of claim 20 wherein said fluid conducting means is circular in shape.

* * * * *

UNITED STATES PATENT AND TRADEMARK OFFICE
CERTIFICATE OF CORRECTION

PATENT NO. : 5,720,078

DATED : February 24, 1998

INVENTOR(S) : J. Aaron Heintz

It is certified that error appears in the above-identified patent and that said Letters Patent is hereby corrected as shown below:

In Col. 8, line 62, add a -- , -- after "bottom".

Signed and Sealed this

Fourteenth Day of December, 1999

Attest:

Q. TODD DICKINSON

Attesting Officer

Acting Commissioner of Patents and Trademarks